United States Patent
Hartwig et al.

(10) Patent No.: US 10,165,988 B2
(45) Date of Patent: *Jan. 1, 2019

(54) PERSONALIZED DETECTION SYSTEM FOR DETECTING MAGNETIC OBJECTS IN THE HUMAN ORGANISM

(71) Applicants: EVONIK ROEHM GmbH, Darmstadt (DE); Gabriele Wersin, Nienhagen (DE)

(72) Inventors: Benedikt Hartwig, Darmstadt (DE); Peter Niepoth, Gross-Umstadt (DE); Hans-Joachim Stiller; Steffen Junginger, Rostock (DE)

(73) Assignee: EVONIK ROEHM GmbH, Darmstadt (DE)

( * ) Notice: Subject to any disclaimer, the term of this patent is extended or adjusted under 35 U.S.C. 154(b) by 564 days.

This patent is subject to a terminal disclaimer.

(21) Appl. No.: 14/899,400

(22) PCT Filed: Jun. 6, 2014

(86) PCT No.: PCT/EP2014/061773
§ 371 (c)(1),
(2) Date: Dec. 17, 2015

(87) PCT Pub. No.: WO2014/202404
PCT Pub. Date: Dec. 24, 2014

(65) Prior Publication Data
US 2016/0135759 A1 May 19, 2016

(30) Foreign Application Priority Data
Jun. 20, 2013 (DE) .................. 10 2013 211 703

(51) Int. Cl.
*A61B 5/05* (2006.01)
*A61B 5/00* (2006.01)
(Continued)

(52) U.S. Cl.
CPC ............. *A61B 5/7475* (2013.01); *A61B 5/05* (2013.01); *A61B 5/4205* (2013.01);
(Continued)

(58) Field of Classification Search
CPC ....... A61B 5/7475; A61B 5/4205; A61B 5/05; A61B 5/6804; A61B 2562/0223;
(Continued)

(56) References Cited

U.S. PATENT DOCUMENTS

| | | | | |
|---|---|---|---|---|
| 6,082,366 A | * | 7/2000 | Andra | A61B 5/06 128/899 |
| 2001/0026222 A1 | * | 10/2001 | Canady, Jr. | A61B 5/06 340/573.1 |

(Continued)

FOREIGN PATENT DOCUMENTS

JP   2009-535103 A1   10/2009

OTHER PUBLICATIONS

International Search Report dated Aug. 27, 2014, in PCT/EP2014/061773 filed Jun. 6, 2014.
(Continued)

*Primary Examiner* — Sanjay Cattungal
(74) *Attorney, Agent, or Firm* — Grüneberg and Myers PLLC

(57) ABSTRACT

The invention relates to a device with a sensor arrangement, which is able to detect magnetic or magnetized oral administration forms after oral take-up, moreover tracks the dissolution thereof via the reduction or disappearance of the magnetic field of the oral administration form, and with a log function, which records a subjective evaluation on the part of the human wearer of the sensor arrangement during or after the oral take-up.

10 Claims, 4 Drawing Sheets

(51) Int. Cl.
    *G01R 33/09*     (2006.01)
    *G01V 3/08*     (2006.01)
    *A61J 3/00*     (2006.01)

(52) U.S. Cl.
    CPC ............ *A61B 5/6804* (2013.01); *A61J 3/007* (2013.01); *G01R 33/096* (2013.01); *G01V 3/081* (2013.01); *A61B 2562/0223* (2013.01); *A61B 2562/04* (2013.01)

(58) Field of Classification Search
    CPC ..... A61B 2562/04; A61J 3/007; G01V 3/081; G01R 33/096
    USPC ........................... 600/407–430; 324/318–322
    See application file for complete search history.

(56) References Cited

U.S. PATENT DOCUMENTS

| | | | |
|---|---|---|---|
| 2007/0167743 A1* | 7/2007 | Honda | ................... A61B 1/041 600/424 |
| 2010/0322859 A1 | 12/2010 | Jones et al. | |
| 2011/0244599 A1* | 10/2011 | Whig | ..................... B82Y 25/00 438/3 |
| 2011/0275907 A1 | 11/2011 | Inciardi et al. | |
| 2012/0317064 A1 | 12/2012 | Hagiwara et al. | |

OTHER PUBLICATIONS

Hu, et al., "A Cubic 3-Axis Magnetic Sensor Array for Wirelessly Tracking Magnet Position and Orientation," IEEE Sensors Journal, vol. 9, No. 5, May 1, 2010, pp. 903-913, XP011306917.

* cited by examiner

PERSONALIZED DETECTION SYSTEM FOR DETECTING MAGNETIC OBJECTS IN THE HUMAN ORGANISM This application claims priority to German Patent Application No. 10 2013 211 703.5, filed Jun. 20, 2013.

FIELD OF THE INVENTION

The invention relates to a device with a sensor arrangement, which is able to detect magnetic or magnetized oral administration forms after oral take-up, moreover tracks the dissolution thereof via the reduction or disappearance of the magnetic field of the oral administration form, and with a log function, which records a subjective evaluation on the part of the human wearer of the sensor arrangement during or after the oral take-up.

Discussion of the Background

In the prior art, examining the cause of a disease, allergy or lack of well-being in the human is linked to an inpatient examination, to the use of an in-situ set of instruments and to a short period of time, during which the set of instruments is used and the human is under medical supervision. Instead of a medical practitioner, it is also possible to look up any other specialized person who maintains or reinstates the sense of well-being of the human, e.g. a pharmacist or therapist in any field.

Patent document U.S. Pat. No. 7,698,156 B2 discloses a device for registering medical data and a method for uniquely identifying the data streams. It renders it possible to distinguish between data streams generated by individual medical instruments, to record said data streams, transmit these wirelessly and thereby provide a basis for a diagnosis and/or medication of the patient. However, the device is stationary, it only measures the bodily functions of the patient and, optionally, registers these together with the time, e.g. the date. Moreover, conventional technical aids do not register anything additionally; a person skilled in the art would not expect anything else either. Particularly in the period of time before use is made of this prior art, there is a lack of reliable statements relating to which relationships exist between the sense of well-being of the human and measurable variables or temporally registerable circumstances.

A challenge can be seen in the fact that the human must always initially be made aware of a risk to his health or an impairment of his sense of well-being, before he perceives a reason to subject himself to an examination and measurement of his bodily functions and to request a diagnosis. This challenge can be refined by the question to what extent health and/or sense of well-being are connected to his lifestyle, in particular to his food and the take-up of food supplements, stimulants, drugs, and also homoeopathic substances and/or medicaments.

SUMMARY OF THE INVENTION

It was therefore an object of the invention to provide a device enabling the registration of such relationships, and a method, with the aid of which it is possible to evaluate such relationships.

Surprisingly, this object was achieved by means of a device comprising the detector system presented in the patent application DE 10 2011 089 334.2 and, additionally, a log which is provided for registering a quantified evaluation before, during and/or after registering the magnetic body or bodies.

Therefore, the subject matter of the invention is a device, comprising a detector system for registering magnetic bodies in the human organism, which detector system comprises at least two sensor arrangements with an instrument for recording the magnetic flux density measured by each sensor arrangement, wherein each sensor arrangement has one, two or three anisotropic magnetoresistance sensors, the axes of easy magnetization of which point in pair-wise different directions, and each sensor arrangement has a distance of 0.5 to 50 cm from the remaining sensor arrangement or sensor arrangements, and at least two sensor arrangements are tilted at an angle of between 0 and 45° with respect to one another, and has a log for registering a quantified evaluation before, during and/or after the registration of the magnetic body or bodies.

An advantage of this device is that it renders it possible to register conscious aspects of the human wearer thereof, namely the quantified evaluation, and at least one objective variable, namely the magnetic flux density measured by the magnetic body.

DETAILED DESCRIPTION OF THE INVENTION

Figure 1:
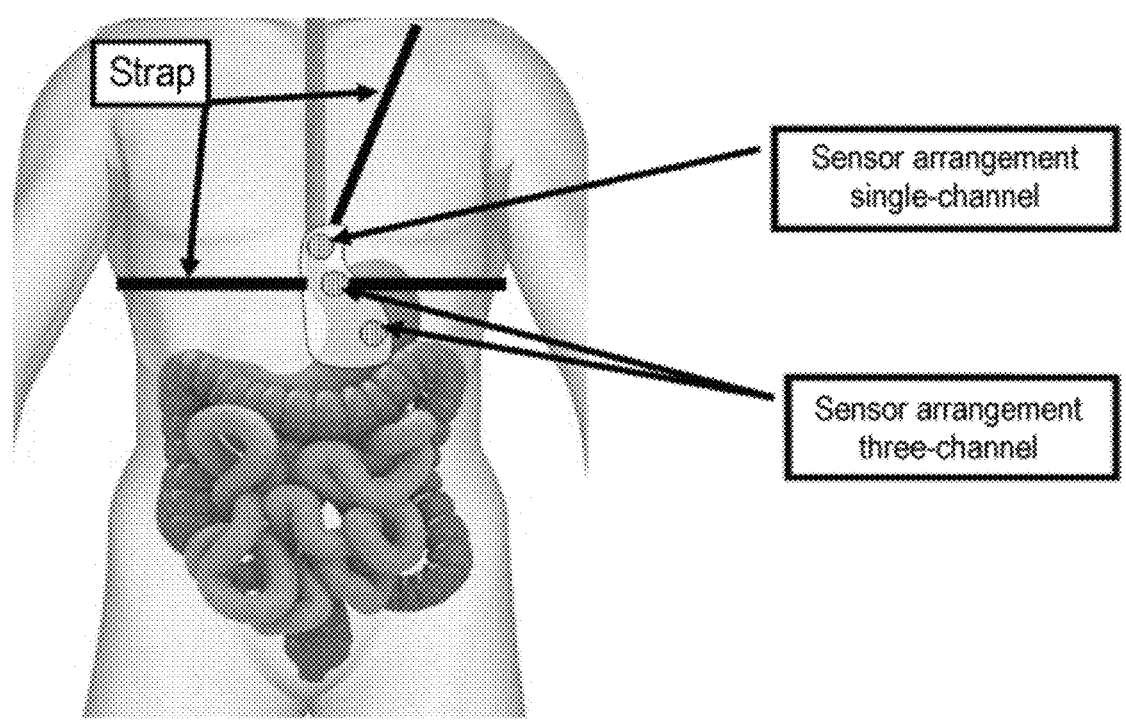
FIG. 1 shows the device according to the invention having three sensor arrangements in a combined chest and shoulder strap, worn on the person.

The invention will be explained in more detail below.

The log of the device according to the invention is provided for entries which are undertaken manually, within the meaning of a digital, electronic diary or notebook, and on his own accord by the wearer of the device according to the invention. The log can be a mobile computer, preferably a commercially available mobile telephone, PDA, small computer, data logger with transmitter, and/or an input unit, wherein the log is electronically connected to the sensor arrangement. Therefore, the human wearer of the device can handle the log in a manner corresponding to the habits of the carrier of a mobile computer.

The log can comprise a Bluetooth interface in order to be able to recall data recorded by the sensor arrangement together with the log entries.

The sensor arrangements of the device according to the invention can be integrated in at least one strap, the clothing and/or an item, or items, of jewellery, or in an armband, e.g. in a wrist watch, or be or affixed directly on the body by means of a suction cup or fastening aid, and the log is also carried on the body. The advantage of such a device lies in the mobility, since the human wearer can carry the device according to the invention with him in all daily activities, without restricting his mobility.

In a particularly preferred manner, the strap in which the sensor arrangements can be integrated can be put on the human without the aid of a third party. This strap can be, for example, a belt, which restricts its wearer only minimally in his everyday movements. Advantageously, the strap may be a combined chest and shoulder strap. Particularly advantageously, the combined chest and shoulder strap can be a strap system which is known from the sport of climbing. An advantage of the combined chest and shoulder strap lies in positioning the sensor arrangements with high precision relative to the oesophagus and the gastrointestinal tract. The strap system additionally has the particular advantage of keeping the sensor arrangements of the device according to the invention particularly accurately respectively at a defined distance and the axes of easy magnetization thereof at a defined angle. The strap permits its wearer full mobility during everyday tasks, in particular during actions at work and leisure. The device according to the invention can also be carried along on any article which is in the vicinity of the body or carried along on the body of the person, for example fitted to a wheelchair, walker, a cradle, couch, or to crutches, or integrated in a wrist watch, in an armband, chain or item of jewellery.

If a sensor arrangement of the device according to the invention has only one AMR sensor, this is also called "single-channel" in the context of the invention; in the case of three AMR sensors, accordingly "three-channel". By way of example, if a sensor arrangement has three AMR sensors, the easily magnetizable axes of which are arranged like the coordinate axes x, y and z of a Cartesian coordinate system, the components of the vector of this sensor arrangement are the measurement signals, the signals $S_x$, $S_y$, and $S_z$ in the x, y and z direction, respectively. They are the measure for the magnetic flux density in the direction of the coordinate axes.

The axes of easy magnetization of a sensor arrangement meet at an imaginary point, the origin of the respective sensor arrangement. The distance between these origins or, in the case of three sensor arrangements, the pairwise distance between these origins, within the context of the invention is the distance or the pairwise distance between the sensor arrangements.

The axes of easy magnetization of the second sensor arrangement each lie parallel to the coordinate axes x, y and z or at an angle thereto. Within the context of the invention, this angle is defined as follows: The axes of easy magnetization of each sensor arrangement lie on a respective imagined conical surface of a solid angle. Within the context of the invention, the angle at which the two sensor arrangements of the detector system according to the invention are tilted with respect to each other is the angle between the central axes of the cone of the sensor arrangements.

If the detector system is carried along in a strap, armband or object in the vicinity of the body, within the context of the accuracy with which the strap can be adjusted, the angle lies in the plane which is defined by the origins of the sensor arrangements and the point of entry of the oesophagus into the stomach. Particularly high accuracies are achieved if this object is a strap system known from the sport of climbing.

If the device according to the invention has two sensor arrangements, the directions and the signals are numbered consecutively. Accordingly, the signals $S_{x1}$, $S_{y1}$, and $S_{z1}$, and $S_{x2}$, $S_{y2}$, and $S_{z2}$, from which the vectors $S_1$ and $S_2$ are formed, are obtained in the directions x1, y1, z1 and x2, y2, z2, respectively:

$S_1=(S_{x1}, S_{y1}, S_{z1})$, and $S_2=(S_{x2}, S_{y2}, S_{z2})$.

If, for example, the first of the sensor arrangements of the device according to the invention has only one AMR sensor, namely in the direction x1, the vector $S_1$ is simplified to $S_1=(S_{x1}, 0, 0)$.

The device according to the invention has the advantage of measuring these vector components so accurately in each case and making them evaluable in such a way that, during the movement of the sensor arrangement by the wearer, the fluctuation in the magnitude of these vectors remains small or is known to such an extent that the change in the measured values caused by a magnetic body is detected. Thus, the influence of external interfering sources is detected and eliminated or can be filtered out of the measured signal.

The magnitudes of the vectors, abbreviated to $|S_1|$ and $|S_2|$, are calculated in a known fashion:

$|S_1|=(S_{x1}^2+S_{y1}^2+S_{z1}^2)^{1/2}$, $|S_2|=(S_{x2}^2+S_{y2}^2+S_{z2}^2)^{1/2}$.

In the case of a small distance between the sensor arrangements, the same measured values emerge in homogeneous fields. A magnetic body having low magnetic induction in the vicinity of the sensors, as a result of the magnetic field thereof decaying quickly with the distance from the sensor, influences the measured values thereof differently at different distances from the sensors. However, since each sensor arrangement supplies a vector which is composed of the measured signals from the AMR sensors, the device according to the invention has the advantage that the proximity of the magnetic body to the sensor arrangements has an effect on the angle between the measured vectors. This angle changes if the magnetic body moves.

The measuring sensitivity can be increased by advantageous embodiments of the device according to the invention.

Preferably, at least one, preferably each AMR sensor of the device, has 4 barber pole elements, which are connected together to form a Wheatstone bridge or a Wheatstone bridge equivalent circuit. The axis of easy magnetization then is the result from the axes of easy magnetization of the individual barber pole elements. External magnetic fields detune such a Wheatstone bridge much more strongly than e.g. a resistance bridge with only one barber pole element and three conventional ohmic resistances. Accordingly, the sensitivity of a Wheatstone bridge made of 4 barber pole elements is increased.

In specialist circles, it is known that the characteristic curve of the AMR sensor can be changed by intense magnetic fields, since domains of the anisotropic material are reformed or deformed, or because the walls thereof in the material are displaced. This effect can be counteracted by at least one set and/or reset pulse, which is output once before the measurement, preferably multiple times during the measurement, particularly preferably periodically during the measurement, via a set-reset strap. The action of periodically output set and/or reset pulses consists in ensuring the optimal characteristic curve of the AMR sensors.

Alternating the set and reset pulse, called "flipping" within the context of the invention, permits the elimination of offset errors by means of forming the difference between the signals measured after each pulse. Furthermore, thermal, electrical and/or those influences which, for example, occur during the heating of the AMR sensor are eliminated.

Likewise, by using the flipping, automatic adjustment of the working point of the following amplifier is made possible, which, within the scope of the invention, is called "switching feedback". In addition to the mark/space ratio, reliable achievement of the saturation induction by the set and reset pulses is also important.

When forming the difference, the working point for the following amplifier must be adjusted. Inaccuracies in this adjustment in the case of a very large modulation range have an effect as a result of an asymmetrically establishing limitation of the signal.

In addition, the detector system according to the invention can have an offset strap. The current through the offset strap can be supplied by a driver circuit, which may e.g. contain a bridge-connected amplifier as an important element. The offset strap permits the compensation of the field component to be measured by generating a field having an opposed orientation. Without an offset strap, during the measurement of the magnetic flux density, the non-linearity of the sensor characteristic curve and, in addition, the cross-sensitivity of the AMR sensors has to be taken into account. The cross-sensitivity consists in the action of high values of the magnetic flux density in both an axial direction and also on the measured value from an AMR sensor oriented orthogonally thereto.

With an offset strap, however, the bridge voltage of the sensor in a control loop is minimized by feeding a current into the offset strap. The current required for the bridge compensation in the offset strap is a measure of the field to be measured. As a result, measurements are always made at that working point of the sensor characteristic curve at which the sensitivity and linearity have their maximum and, at the same time, the cross-sensitivity vanishes. The detector system according to the invention is therefore suitable for any everyday environment.

The offset strap is connected to the "offset strap driver". In general, non-linearities and cross-sensitivities can be registered during the calibration and the measurement result can be corrected accordingly. As a result, operation without activating the offset strap is also possible, with minimized energy consumption.

There is a further alternative to the compensation of the field component to be measured by generating a field with opposite orientation by means of feeding a current into the offset strap. In this case, at least one, preferably every AMR sensor of the device according to the invention, can be equipped with an alternative circuit.

In this embodiment of the device, the bridge voltage from the sensor is not controlled out to the setpoint value zero in a negative feedback circuit. Instead, by means of a DA converter and an amplifier, a defined current is fed into the offset strap in such a way that there is no departure from a specific modulation range of the sensor bridge.

In a further possible way of implementing the device according to the invention, the modulation range of the sensor characteristic curve can be subdivided into a number of segments, for example into 256 segments in the case of a DA converter having 8 bit resolution. In order to ensure a continuous measurement with a changing magnetic field strength, the segments can be chosen in such a way that there is a sufficient overlap of adjacent segments. Each of these segments can then be provided with only a small modulation range around the optimal working point of the AMR sensor. The reduction in the modulation range reduces the cross-sensitivity and the effects of non-linearities of the characteristic curve. Complete correction of non-linearity and cross-sensitivity is dispensed with. For this purpose, however, improved amplitude resolution of the measurement is obtained by means of the combination of AD converter and segmentation of the characteristic curve.

For this purpose, for each of the segments of an AMR sensor measuring range, the parameters of the approximation by a straight line in each case, together with their associated slope and height section, must be determined. The slopes and height sections of the segments are provided via the calibration data of the sensors. If the detector system according to the invention is moved only during daily use, for example by the everyday movements of its wearer, then the defined current and therefore the approximation are continuously tracked.

Depending on the speed at which the movements are made, a high sampling rate is advantageous, so that a continuous measurement is implemented without any overloads. The advantage of this variant consists in the fact that, given appropriately fast sampling, the offset straps have to be operated with only a very small mark/space ratio. As a result, the power demand and the inherent heating of the sensors and offset problems associated therewith are reduced sharply.

In addition, by using fast AD and DA converters at the measuring frequency necessary for the continuous measurement in the magnetic field, the time needed for the individual measurement can be kept low. It is therefore possible to activate the offset straps only during the time necessary to acquire the measured value. If the activation of the offset straps is carried out, for example, only with a mark/space ratio of 0.1, for example with a 1 ms measuring period and a time interval of 10 ms between successive measurements, then the power loss is reduced. As a result, less heat is developed and thus the drift of the measured signals is reduced or even suppressed.

For the usability of the device according to the invention having two sensor arrangements, care must be taken that the oesophagus has a length of 20 to 30 cm and is passed through in 5 to 10 seconds by a swallowed object. This results in a speed range during the oesophagus passage of 2 to 6 cm/s and therefore a correspondingly rapidly changing signal for the detector system. The frequency range of the useful signal therefore coincides with the frequency range possessed by some of the external interference signals. Within the context of the invention, "external interference signals" denotes those signals which are caused by magnetic fluxes which surround the wearer and in which he—necessarily—moves, for example in the Earth's magnetic field or in the surroundings of magnetic objects such as, for example, vehicles. Because of external interference signals, no ability to distinguish between a passage of a magnetic object through the oesophagus and magnetic fluxes from other objects would be expected. In particular, filtering of the measured signal in accordance with prior art does not lead to success.

One possible way to rule out external interference is offered by the evaluation of autocorrelation and cross-correlation functions of sensors which are positioned at a fixed distance from one another. The cross-correlation describes the correlation of two signals as a function of the time shift between these signals. In the case of autocorrelation, the correlation of a signal with itself is calculated. The autocorrelation function always has a maximum at displacement 0. If a signal with a delay is picked up by two otherwise equal sensors, the maximum of the cross-correlation function with an otherwise equal shape is displaced by the delay with respect to the maximum of the autocorrelation functions.

One essential precondition for the identification of the passage of a capsule through the oesophagus is that the sensor arrangements are able to detect a time-offset component of the signals. The problem which remains, however, is caused by the movement of the sensor arrangement in the surrounding Earth's magnetic field, which certainly matters to the usability of the device according to the invention.

Despite the multiplicity of magnetic fluxes from numerous objects, for example from vehicles, metallic furniture, power-carrying lines and the like, the device according to the invention unambiguously detects such fluxes which originate from the magnetic body in the human organism if the distance between two sensor arrangements is chosen to be from 2 to 6 cm.

By means of unequal locations of the sensor arrangements, external magnetic fields which do not originate from the magnetic body in the human organism are detected. The sensor arrangements are preferably fixed vertically or horizontally over oesophagus or breastbone and stomach. FIG. 1 shows the device according to the invention having three sensor arrangements in a combined chest and shoulder strap, worn on the person. The log and the instrument or instruments for recording the magnetic flux density measured by each sensor arrangement are not depicted. In this exemplary embodiment, the sensor arrangement in the vicinity of the oesophagus has a single channel; on the other hand the two other sensor arrangements are implemented with three channels. The solely single-channel design of the sensor arrangement in the vicinity of the oesophagus simplifies the construction and reduces the power demand of the device according to the invention. In addition, this single-channel embodiment makes use of the possibility that the magnetic body does not have to be designed spherically symmetrically but, for example, can be designed cylindrically symmetrically, and the magnetic field generated by the same moves as a result relative to the single-channel sensor arrangement without rotating during the passage through the oesophagus.

It can also be advantageous to remove the proportion of the interfering surrounding fields by means of the subtraction of a moving average and to choose the distance between the sensor arrangements to be 2 cm. By using the filtered signals, the autocorrelation and cross-correlation functions thereof can then be calculated. By using the differences between the amplitudes and the position of the maxima, the passage of a magnetic body can then be detected.

If the device according to the invention has two or three sensor arrangements, it can be used to detect the magnetic body in the stomach.

The slow disintegration of the magnetic body leads to the weakening of the magnetic flux density thereof. Movements of the wearer and positional changes of the magnetic body, for example as a result of peristalsis, lead to fluctuations in the measured value. Although, in general, no statements are possible about the superposed movement pattern of peristalsis and magnetic body, the device having three sensor arrangements leads to success. It is further advantageous to equip the device with low-pass filtering as a measure for signal processing.

The magnetic body can be embodied in such a way that it can be administered via oral ingestion, in particular swallowed by the person. The configuration of this magnetic body will also be called "oral administration form" within the context of the invention. This can be a capsule or a capsule with function, wherein the function is chosen from diagnostic and/or pharmacological form. The capsule can furthermore preferably be a tablet, which preferably passes the oesophagus in the longitudinal direction. The administration form has at least one magnetic component, preferably a paramagnetic, super paramagnetic, ferrimagnetic and/or ferromagnetic component, preferably at least one core and/ or shell containing magnetite. The magnetic component can have magnetically orientable or magnetizable particles, preferably magnetite ($Fe_3O_4$) or maghemite ($Fe_2O_3$). Magnetite and maghemite count as toxicologically and pharmacologically harmless and, amongst other things, are used as non-toxic, insoluble pigments in foodstuffs or pharmacological forms.

Optionally, other magnetically orientable particles such as ferrite $MnFe_2O_4$ or $MgFe_2O_4$ can also be suitable. The magnetic proportion of the magnetic body can lie in the range from 0.05 to 80 mg, preferably from 2 to 70, preferably 4 to 60, in particular 6 to 50 mg, of magnetically orientable or magnetizable particles. The average particle sizes of the magnetically orientable particles can lie, for example, in the range from 1 nm to 1 mm, preferably from 100 nm to 100 μm.

The oral administration form can likewise preferably be a capsule, a tablet, a small rod, a coated tablet, a melt extrudate or a body having an incorporated magnetic film.

Therefore, the device according to the invention, in which a sensor arrangement is oriented orthogonally with respect to the main axis of the administration form, detects a marked change in the measured value during the passage of said administration form.

The time scale and the spatial scale on which the measured signals, at least from the two sensor arrangements, lie are given by the speed with which the oral administration form passes the detector system according to the invention, and by the spacings or pairwise spacings of the sensor arrangements. Although, as already stated above, a multiplicity of magnetic flux densities are superimposed and the actual flux density of interest is very small and inhomogeneous over time and space, it has been recognized that this can be detected reliably by the detector system according to the invention.

Since the device according to the invention has a log, it is possible, together with the flux densities of interest, likewise to register subjective entries in a timely manner and/or simultaneously with the passing of the oral administration form.

Therefore, a subject matter of the invention is likewise a method for registering the magnetic flux density generated by a magnetic body in the human organism by means of the device according to the invention, which is characterized by the steps:
(a) applying a set and reset pulse, at least once, to each anisotropic magnetoresistance sensor,
(b) amplifying the signals of each AMR sensor by means of suitable signal conditioning and by means of at least one low-pass filter,
(c) determining and recording the difference in the magnitudes of the vectors of the magnetic flux densities of each sensor arrangement, and/or determining and recording the angle φ between the vectors from the measurement signals of the AMR sensors, and,
(d) simultaneously with one of the steps (a), (b) or (c) or after a time T has elapsed following step (c), registering the quantified evaluation, at least once, in the log, which is undertaken by the human wearer of the sensor arrangements.

The method is advantageous not only by virtue of reducing dynamic bothersome influences when registering measured values by virtue of reducing the falsification of offset values, e.g. as a result of passing vehicles, or the transient or decaying properties of employed filters. The method according to the invention has the additional advantage of enabling simultaneous and/or timely registration of subjective criterion correlations, which are not accessible on the basis of objective measurement data alone.

In step (a), the set and reset pulses are applied alternately, which equally means that these are applied cyclically. They should be output with a current pulse intensity at which saturation magnetization is achieved in each case, and therefore the slope of the characteristic curve is controlled. The current pulse intensity fluctuates in a way known to those skilled in the art, depending on the component.

In step (b), Gauss filters, Bessel filters can preferably be used to suppress overloads or waviness in the signal. In order to separate fast and slow changes in the signals, band pass filters known to those skilled in the art are a preferred type of signal conditioning. Periodic electromagnetic interference having frequencies of 16.7 Hz, for example in the case of electrified rail operation, or 50 Hz, the mains frequency, can be suppressed by choosing the sampling rate and the integration time of 60 ms or multiples during the data acquisition. The integration time has to be matched accordingly in the event of differing frequencies of the periodic interference.

In order to filter out electromagnetic interference radiation from the frequency ranges from 16 to 50 Hz, preference is given to 2 arrangements, in which the integration constant is at least 60 ms. Preferably, in this way the sampling frequencies are matched to different periodically occurring interference sources.

The measure of the magnetic flux density in the x, y and z direction in step (c) is the voltages dropping in the respective direction from the detuning of the Wheatstone bridges of the AMR sensors. The person skilled in the art will assume that, in the difference $\Delta_0$ between the vectors from two sensor arrangements, $$\Delta_0 = S_1 - S_2,$$

the proportions of homogeneous magnetic flux densities just cancel out. The influence of interfering external fields, barely variable in space, would therefore be compensated, and there would only remain substantially the field from the magnetic body in the wearer. However, the two sensor arrangements must not be tilted or tilted only a little with respect to each other, equivalent to the angle 0°. Magnetic flux densities of events offset in space and time are, however, surprisingly detected even at larger angles if, instead of $\Delta_0$, the scalar value $\Delta$ is formed:

$$\Delta = |S_1| - |S_2|$$

This simplifies the mounting of the sensor arrangements in the strap of the device according to the invention and, in addition, saves tedious adaptations in the position of the sensor arrangements to different proportions of the wearer. In a graph of the value $\Delta$ as a function of time, characteristic line forms are thus detected and, for example, are assigned to the swallowing of the magnetic body, the passage of the latter through the oesophagus, thus the passage of the sensor arrangements, and the movements of the latter on account of the peristalsis during the digestion.

In order to be able to perform this assignment, the filtering of the measured signal is not adequate. Although the prior art knows an option for switching-off external influences by evaluating autocorrelation and cross-correlation functions of sensors which are positioned at a fixed distance from one another, if a signal with a delay is picked up by two otherwise equal sensors, the maximum of the cross-correlation function with an otherwise equal shape is displaced by the delay with respect to the maximum of the autocorrelation functions. In order that a time offset between autocorrelation and cross-correlation of the sensor signals can now be detected, the proportion of the signal caused by the oral administration form must not be covered by external magnetic fields. To this end, however, the external interference would largely have to be eliminated. For this purpose, for example, the formation of the difference between the current signal and an average is used. This average must be matched to the current situation and, for example, be obtained as a so-called "moving average". However, this means that, during the ingestion of the oral administration form, the test person completes neither rapid rotational nor rapid translational movements of large amplitude. Only then will sensors according to the prior art ensure adequate signal separation.

Of course, the sampling rate can also be increased, so that a continuous measurement would be implemented without any overloads. It is possible to compensate, at least partly, for the disadvantage of an energy demand that would then be increased, by high sampling rates only being set in the case of interesting, complex events, such as for example during swallowing and/or the disintegration of the magnetic body. Such interesting, complex events must be detected by the system, however. However, this is brought about by the device according to the invention, namely on the basis of registering the precise time of take-up and, if the human wearer provides this, on the basis of at least one entry in the log. It is even possible to correlate the problem, known in the prior art, that fast rotational and/or translational movements with a large amplitude, which are not associated with the oral administration form, continue to be visible in the measured signals with an entry or entries into the log. Thus, further information is available about the surroundings of the wearer and, likewise, about the circumstances of taking oral administration forms, and/or information about how interference not associated with the oral administration form is to be compensated for.

The alternative calculation of the angle φ enclosed by the measurement signal vectors in accordance with formula I, $$\phi = \arccos(S1 \cdot S2 / |S_1||S_2|), \quad \text{I}$$

in step (c) of the method is an alternative for circumventing the aforementioned problem. We found that rapid movements of the wearer and/or rapid external flux changes of the interfering fields act less significantly on the relative orientation of the measured signal vectors in relation to one another than the movement of the magnetic body in the carrier organism. This can be explained by the sources for external flux changes deflecting both the measured signal vectors or, in the case of three sensor arrangements, three measured signal vectors, in at least approximately the same directions. Although the magnitudes thereof can quite possibly be changed differently, the angle between two pairs of the measured signal vectors in each case, based on the time, must remain approximately the same. This is equivalent to the surrounding magnetic field from further removed sources approximately maintaining its homogeneity or inhomogeneity. I accordingly permits further removed sources of magnetic fluxes to be masked out, irrespective of their time behaviour.

Figure 2:
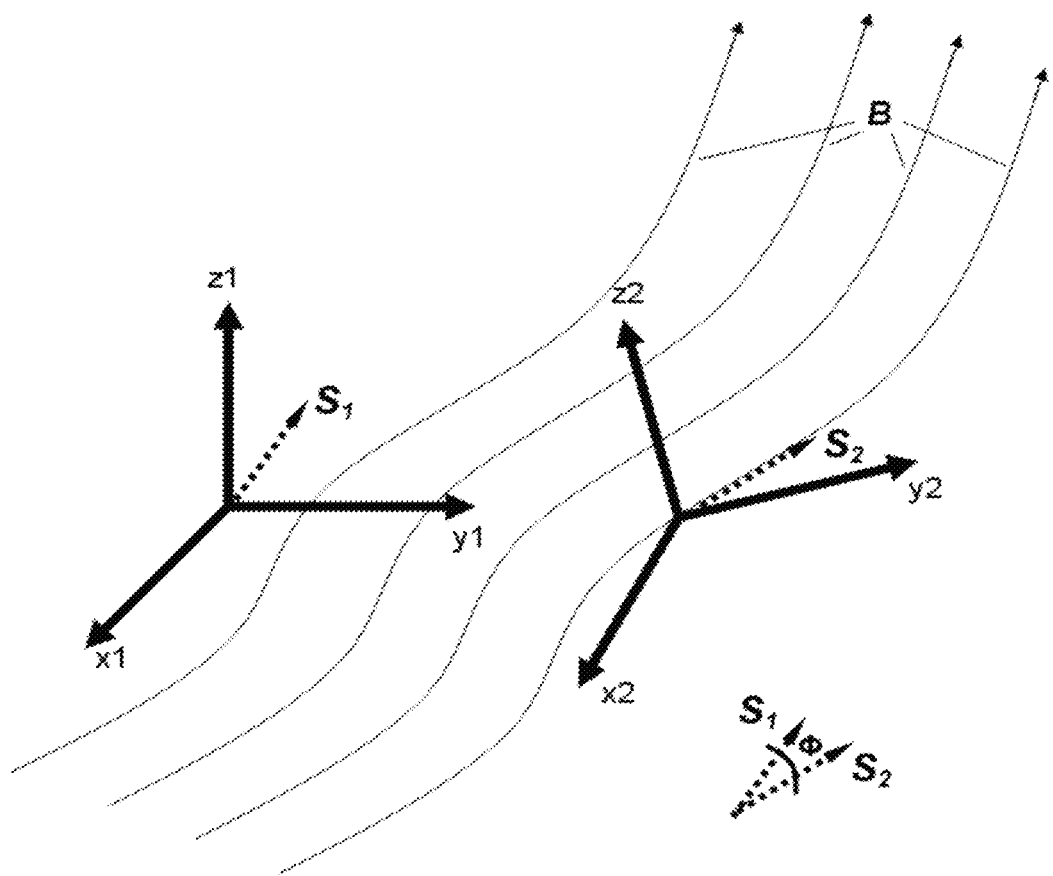
FIG. 2 shows an embodiment of the invention schematically.

The situation when carrying out the method according to the invention is schematically shown in FIG. 2. The meaning of the reference signs is the following:

B Field lines of the interfering magnetic flux
$S_1$, $S_2$ Vectors $S_1 = (S_{x1}, S_{y1}, S_{z1})$ and $S_2 = (S_{x2}, S_{y2}, S_{z2})$
φ angle enclosed by the measured signal vectors in accordance with formula I.

Under the assumption that sources of the interfering magnetic flux are physically further removed than the magnetic body or the oral administration form, the angle between the vectors $S_1$ and $S_2$ is approximately constant over time. In the best case, namely in a homogeneous magnetic field, this angle even disappears constantly. However, it has been found that interfering magnetic fields are often substantially homogeneous. One advantage during the determination of the angle $\phi$ is the unimportance of erroneous orientation of an individual AMR sensor or all the AMR sensors or the tilting of the sensor arrangements with respect to one another, if this erroneous orientation is constant over time. Such an error manifests itself in an insignificant offset in the $\phi/t$ graph, equivalent to $$\phi = \text{const}$$

with respect to the time t.

In the method according to the invention, in step (b), it is possible to use at least one low-pass filter having the cut-off frequency of 0.1-0.99 mHz, 1 mHz-0.99 Hz, 1 Hz-9.99 Hz, 10 Hz-1 kHz, or a combination of low-pass filters having at least two different cut-off frequencies. In this case, it is preferable to adapt the filtering to the process to be detected, in order to suppress noise and/or rapidly changing interference fields, for example from electrical appliances, in the measured signal.

In the method according to the invention, the magnitude of each AMR sensor or the measured signal obtained in step (c) can be filtered by a median filter.

Furthermore, in the method according to the invention, during the performance of step (c), the variable $\Delta$ and/or $\phi$ that is obtained can be recorded as a function of time by means of a data logger or another suitable device known to those skilled in the art, with which the device according to the invention is equipped. This recording can be carried out continuously, for example during the ingestion, the passage and/or the disintegration of the magnetic body in the organism of the wearer. It can also be carried out discontinuously, in order for example to save energy.

It was found that many everyday sources of interfering fields produce characteristic line forms in the $\Delta/t$ or $\phi/t$ graphs. Thus, for example, motor vehicles travelling past, electrical switching operations, electromagnetic interference caused by sparks and also stochastically periodic interference and/or brush sparking from electric motors can be detected in the graph and it is possible to compensate for the contribution thereof to the line form by means of software known to those skilled in the art.

The method according to the invention can advantageously also be used when the magnetic body is already located in the stomach and disintegrates there. The magnetic body can also disintegrate in the intestines or in the colon. In these cases, digital filtering in the range from 0.1 to 1 mHz is preferred. If the swallowing process is to be detected, a low-pass filter having a cut-off frequency range from 1 mHz-0.99 Hz is preferred. Furthermore, it can be advantageous to adapt the choice of filters and/or cut-off frequencies to the geometric structure of the magnetic body, in particular the oral administration form. The time period in which an oral administration form, for example a capsule, disintegrates lies in the range from 0.5-30 min, preferably in the range from 0.5-20 min, further preferably in the range from 0.5-5 min. If such long-lasting processes in the human body are to be measured, the signals can preferably be "smoothed exponentially". The mathematical procedure for this is known to those skilled in the art. Preferred smoothing constants $\alpha$ lie in the range from 0.10 to 0.40; particularly preferably $\alpha$ is approximately or equal to 0.25.

The magnetic body of the administration form of the device according to the invention has subunits, which can be layers, phases and/or domains. That subunit which produces the magnetic flux has inert, crystalline particles, which can be particles, glazed and/or encapsulated micro and/or mini magnets. The micro and/or mini magnets preferably have the form of cylinders, shells and/or spheres.

Figure 3:
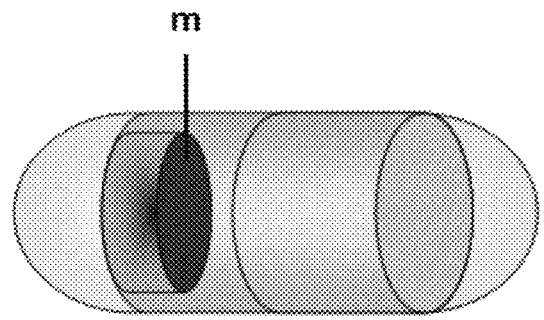
FIGS. 3A-3C show preferred embodiments of the magnetic body, specifically in the form of a capsule, which is respectively equipped with one (FIG. 3A), two (FIG. 3B) or three (FIG. 3C) mini magnets (m).
Figure 3:
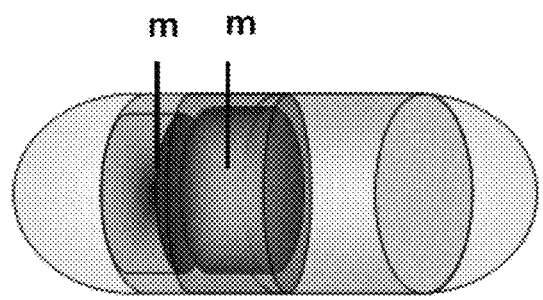
Figure 3:
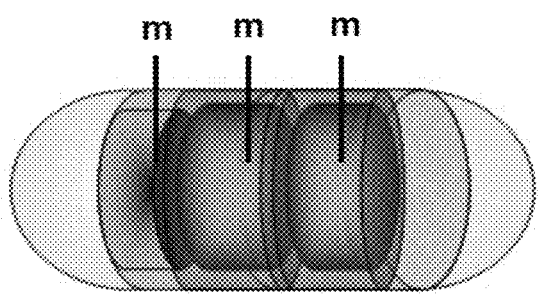

Preferred dimensions of the micro and/or mini magnets are from 0.1 to 1 µm, from 1 to 10 µm, from 10 to 100 µm, from 100 µm to 1 mm and/or from 1 mm to 10 mm. The micro or mini magnets have magnetic particles, preferably made of magnetite and/or a magnetic material which is not metabolized by the human organism. Furthermore, the magnetic particles can have micro-structured polymer composites and/or partially crystalline, polymorphic, sintered, powdery or combinations thereof. The magnetic particles can also have further commercially common components, preferably coated by the latter, for example by dextran particles, or by other components for molecular coating, for example by cyclodextrins, or by components which are obtained by granulation or pelleting methods. If the micro or mini magnets are encapsulated or coated by means of the latter, the systemic absorption of the micro or mini magnets is inherently hindered. Preferably, the disintegration of the micro or mini magnets by the stomach acid is slowed by these and/or the start of the disintegration is retarded. With the progressive disintegration, in turn that magnetic flux weakens until it disappears, which is registered by the detector system according to the invention in accordance with the method of the invention. FIGS. 3A-C show preferred embodiments of the magnetic body, specifically in the form of a capsule, which is respectively equipped with one (FIG. 3A), two (FIG. 3B) or three (FIG. 3C) mini magnets (m).

The magnetic body is preferably produced by means of galenic methods known to those skilled in the art for the production of oral administration forms, for example by means of GMP-capable production methods, preferably for the production of granules by means of a so-called high shear mixer, or in a fluid bed granulator, by means of a roller compactor, an extruder, spheronizator or a hot-melt process. Also preferred is the production of so-called pellets by means of pelletization known to those skilled in the art, extrusion and spheronization, rotary granulation or powder layering. Furthermore, magnetic bodies can be produced in the form of micro tablets from partially crystalline, compressed, encapsulated and/or tableted material, by these being compacted from powder and polymorphic substances. Oral administration forms can also be produced in the form of small envelopes known to those skilled in the art, so-called sachets.

Also conceivable are more complex forms of magnetic bodies, in which, for example, the magnetic component has the form of one or more films. Magnetic bodies of the detector system according to the invention can be obtained in any desired combination of the above-mentioned methods. These can also be multi-particle systems, multi-layered systems, core-shell systems and/or co-block systems.

The oral administration form can have any desired form which has at least one magnetic phase, "magnetic phase" being understood to mean a body delimited physically in the magnetic body which causes a magnetic flux. The latter is detected in accordance with the method of the invention. The oral administration form, following ingestion into the human body, is disintegrated in a defined time period. If, for example, two, three, four or five magnetic phases are contained, these time periods can have different lengths, preferably different lengths in pairs. The different length of the time periods can be achieved, for example, by the magnetic material being coated in a polymer film.

If the oral administration form is a capsule, for example half the capsule can be filled with the magnetic material. Furthermore, the magnetic material pressed into a tablet can be put into the capsule. The magnetic phase can preferably be surrounded by a sheath which is resistant to stomach acid and which coincides with the sheath of the oral administration form or is different from the latter. The functions of such slowly disintegrating sheaths, also referred to as "coatings" or "matrix structures", are known to a person skilled in the art. Naturally, with the onset of the disintegration of the sheaths, there is also an onset of the disintegration of the magnetic material as soon as it comes into contact with the medium which causes or caused the disintegration of the sheath. With the disintegration of the magnetic material, the collective ordering of the electron spins causing the magnetic flux is lost and, with the extinguishing of the collective magnetic ordering, the magnetic flux weakens as far as its inability to be measured or its disappearance.

The material of a slowly disintegrating sheath or encapsulation can be chosen from film-forming polymers. These can be, for example, copolymers of methyl methacrylate and ethyl acrylate, copolymers of methyl methacrylate and ethyl acrylate and methacrylic acid, copolymers of methyl methacrylate and methyl methacrylate and methacrylic acid and copolymers of methyl methacrylate, ethyl acrylate and trimethylammonium ethyl methacrylate.

Suitable in particular are copolymers of the type EUDRAGIT® E100, EUDRAGIT® E PO, EUDRAGIT® L100, EUDRAGIT® L100-55, EUDRAGIT® S, EUDRAGIT® FS, EUDRAGIT® RS or EUDRAGIT® RL, EUDRAGIT® NE or EUDRAGIT® NM.

Also suitable are polyvinyl pyrrolidones (PVP), polyvinyl alcohols, polyvinyl alcohol-polyethylene glycol graft copolymer (Kollicoat®), starches and derivatives thereof, polyvinyl acetate phthalate (PVAP, Coateric®), polyvinyl acetate (PVAc, Kollicoat), vinyl acetate-vinyl pyrrolidone copolymer (Kollidon® VA64), vinyl acetate: crotonic acid copolymers, polyethylene glycols with a molecular weight above 1000 (g/mol), chitosan, a (meth)acrylate copolymer, consisting of 20-40% by weight methyl methacrylate and 60 to 80% by weight methacrylic acid, known as EUDRAGIT® S, a crosslinked and/or non-crosslinked polyacrylic acid, fissure sealer known as Smartseal® based on a composite, salt of alginic acid and/or a pectin, celluloses such as, for example, anionic carboxymethyl cellulose and salts thereof (CMC, Na-CMC, Ca-CMC, Blanose, Tylopur), carboxymethyl ethyl cellulose (CMEC, Duodcell®), hydroxyethyl cellulose (HEC, Klucel), hydroxypropyl cellulose (HPC), hydroxypropyl methyl cellulose (HPMC, Pharmacoat, Methocel, Sepifilm, Viscontran, Opadry), hydroxymethyl ethyl cellulose (HEMC), ethyl cellulose (EC, Ethocel®, Aquacoat®, Surelease®), methyl cellulose (MC, Viscontran, Tylopur, Methocel), cellulose ester, cellulose glycolate, cellulose acetate phthalate (CAP, Cellulosi acetas PhEur, cellulose acetate phthalate, NF, Aquateric®), cellulose acetate succinate (CAS), cellulose acetate trimeliate (CAT), hydroxypropyl methyl cellulose phthalate (HPMCP, HP50, HP55), hydroxypropyl methyl cellulose acetate succinate (HPMCAS-LF, -MF, -HF) or is a mixture of the aforementioned polymers.

In addition to the film-forming polymers, further pharmaceutically usual aids which are not film-forming polymers can be used in a known way as formulation aids or additionally contained. Here, stabilizers, colorants, antioxidants, wetting agents, pigments, glossing agents, etc. can be named by way of example. They are primarily used as processing aids and are intended to ensure a reliable and reproducible production method and good long-term storage stability. Further pharmaceutically usual aids can be present in quantities from 0.001 to 30, preferably 0.1 to 10% by weight, based on the film-forming polymers. Likewise, additives known to those skilled in the art for tablets, capsules or pharmacological forms can be employed.

The oral administration form can furthermore have at least one shell and at least one core, which are the magnetic phases and which are disintegrated from outside to inside in order in the human organism, so that the core or the cores maintains or maintain the magnetic flux for the longest.

For example, the administration form can have a core in the form of a flat tablet, wherein the flat sides of the tablet are the magnetic phase, which is firmly connected, for example fixed chemically or mechanically or fused, to a further substance, and which is intended to be supplied to the human organism. This substance can be, for example, an active substance, a drug or generally a biologically active substance and be present on the inside of a magnetic shell. The magnetic phases of the tablet can have various thicknesses or be coated in various ways by a further material, wholly or partly, so that the magnetic phases disintegrate within time periods of different lengths. These time periods can be chosen such that the magnetic phases disintegrate while the administration form is being transported in the human organism, and thus each magnetic phase disintegrates at a different location in the human organism. For example, a time period can be chosen to be short, with the result that one of the magnetic phases disintegrates as early as during the passage through the oesophagus.

In a further preferred embodiment, the oral administration form can have at least three constituent parts, of which at least one constituent part, preferably each constituent part, encloses a magnetic phase.

The oral administration form can, moreover, have at least three phases, of which at least one phase can have a biologically active substance, and the other phases contain no biologically active substances but one or in each case one magnetic phase. Such administration forms can be produced more simply.

The oral administration form can likewise preferably have a magnetic phase at or on its outer surface. When such an administration form is ingested, the magnetic phase disintegrates first. Only after that do the remaining constituent parts of the administration form come into contact with the human organism. This embodiment has the advantage, not exclusively, that the device according to the invention registers the exact time of the ingestion. The exact time of the ingestion can be detected, for example, by a peak in the time derivative $\partial \Delta / \partial t$ of the measured signal vector difference and/or in a sudden rise in the magnitude of $\partial \phi / \partial t$ above a value which has previously been defined. Within the context of the invention, such a time is equivalent to the detection of changing magnetic fields and thus the detection of the oesophagus passage.

When recording the variable $\Delta$ and/or $\phi$ as a function of time, the detection of the oesophagus, denoted by "oesophagus passage detected", is logically positive. The processing of this and of the following logical state is illustrated schematically in FIG. 4.

If, on the other hand, the time of ingestion is known, it was found as a further advantage of this administration form that various external magnetic fluxes or flux changes which are present at various times and cannot be masked out or calculated out completely in step (b) and/or (c) are nevertheless detected as interfering fluxes, by the line form respectively generated in the Δ/t or φ/t graph by the magnetic flux of the administration form following the ingestion time being used as a respective characteristic for the graph. This can be brought about in that, directly after the first-time ingestion of the administration form, the line form is tabulated during a time interval of 0 to 10 s, preferably of 0 to 5 s, and/or is approximated by suitable mathematical functions. Immediately after each further ingestion, at respectively known times, the line form then detected can be compared with the tabulated or approximated line form. Within the context of the invention, such a comparison is designated by "data recording and data comparison". If the line form detected coincides in its tabulated and/or approximated form with the line form during the first ingestion of the administration form, then this finding, designated by "pattern known", is logically positive. If the logical values oesophagus passage detected and pattern known are positive, the detection according to the method of the invention can be performed, since that which is measured by means of the changing magnetic fields is "pattern detected". Then, however, the further flux changes, which cause the passage of the administration form and the disintegration of the latter in the organism, are detected during various times of the ingestion, despite different surroundings. This results in the further advantage of mobility of the device according to the invention, virtually irrespective of the location or intensity of external magnetic fluxes, since the method according to the invention now even distinguishes between various, unknown external interfering influences. If at least one of the two logical states is negative, the detection can be avoided, the detector system according to the invention can be switched off and/or a further notification, which is matched to the use of the system, can be generated.

In a further embodiment of the method according to the invention, the quantified evaluation can be undertaken by virtue of the fact that at least one subjective criterion, preferably a sense of well-being and/or physical fitness, is assigned to alphanumerical signs, preferably a grade scale, and entered into the log.

Figure 4:
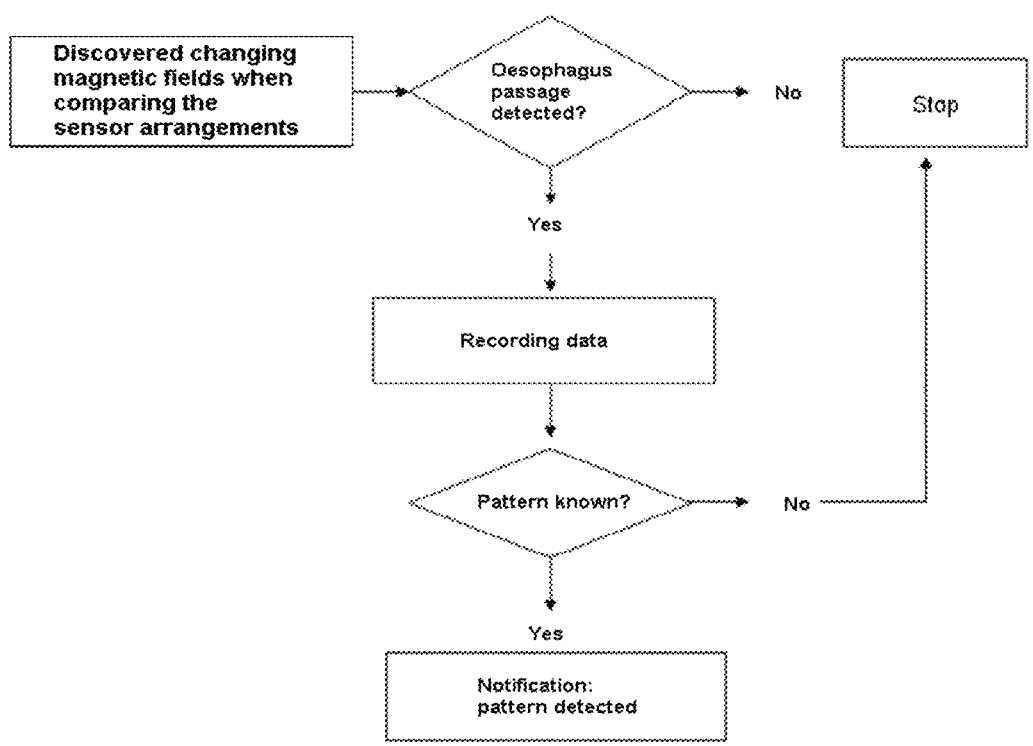
FIG. 4 illustrates the detection of the oesophagus schematically.

The log registers/stores this assignment, for example the sense of well-being expressed in the form of a school grade, together with a logic quality as per FIG. 4, for example "pattern known". It is also possible to detect further data, e.g. date/time, and/or notable occurrences when identifying the oesophagus passage. This can likewise be graded and registered by the human wearer, e.g. particular stressors, or, if this has occurred, it is possible to detect multiple balancing of a registered line form with the tabulated line form as a result of an interference source.

Therefore, the present invention has numerous advantages by virtue of it being possible to obtain many correlations, which only occur in the surroundings of the human wearer and which preferably are only perceived by him.

Even bothersome influences, which are not consciously perceived by him, e.g. large magentic interference fields which lead to multiple balancing of the line forms, can then be correlated with e.g. the sense of well-being and the take-up of the oral administration form.

Moreover, it may be advantageous to record the values for the difference obtained in step (c) and/or for the angle φ as a function of time and the evaluation registered in step (d) as a function of time.

A choice relating to which data are intended to be correlated with one another can be made on the basis of this recording. By way of example, characteristic peculiarities in the Δ/t or φ/t graphs, if present, may be correlated with the subjective criterion as a function of time. Such correlations have not previously been accessible to any data management network, but may provide statements about tolerance, effect, appropriate metering of the oral administration form. Moreover, statements are possible as to whether there even is a relationship between a subjective evaluation and any one of the remaining recorded data.

The subject matter of the invention is likewise the use of the device according to the invention for registering swallowed oral administration forms and determining the time or times of the disintegration of the magnetic, preferably ferromagnetic, component in the digestive tract. The advantage consists in the fact that, at the time at which this component disintegrates, or a defined time period before the same, the magnetic body, generally the oral administration form, likewise disintegrates or must disintegrate, and thus substances enclosed therein must be liberated. The detection of the disintegration can thus be a time marker for when, for example, an active substance reaches a specific part of the human organism. Together with the entry in the log, the use has the further advantage of supplying statements regarding effectiveness and/or suitable application of the oral administration form.

Preferably, during the use according to the invention, the disintegration of the magnetic, preferably ferromagnetic, component in the stomach, large intestine, small intestine and/or colon can be determined. One option of the use according to the invention is as follows.

If the magnetic body has at least two magnetic phases, the disintegration times of which are chosen such that these magnetic phases disintegrate at different locations in the human organism and, in addition, in each case a substance which can be taken up by the human organism and, for example, can be an active substance, a food supplement, a stimulant, a drug or generally a biologically active substance, is firmly connected to each of these magnetic phases, and, with the detection of the respective disintegration, in addition a measurement of the blood level of the substance or substances taken up by the organism is carried out, then, for example in clinical studies, the delivery of this substance or these substances can be correlated in vivo with the behaviour of the metabolism. The device according to the invention can accordingly also be used in therapy and/or diagnostics. The substance taken up by the body can also be a food and stimulant, and thus the detector system according to the invention can be used in all areas of nutrition.

During the use according to the invention, the measured signals and entries obtained in accordance with the method of the invention are stored in at least one data storage device, and the stored data and entries can preferably be transmitted to a receiving device upon the receipt of a request signal.

The device can preferably transmit the signals via a commercially available Smartphone, mobile telephone, PDA, wherein conditioning of the signals can be carried out by a further algorithm on board this small computer. One example of such conditioning can be data reduction, encryption and/or reconciliation with personal data of the wearer. The signals obtained from the device according to the invention can be transmitted on a cable-bound path, for example temporarily by means of a plug-in connection, and/or in a wire-free manner, for example via sensor nodes, computers or by means of Bluetooth® technology to a mobile telephone. If this technology is used, the expenditure for porting the software to the digital signal processor (DSP) can be saved and the processing time can also be shortened.

The data storage device can be a data logger with transmitter which, for example, can be implemented in Bluetooth® technology. It is likewise conceivable to equip the device according to the invention with a data logger with transmitter, or else with a "radio-frequency identification device" (RFID). By means of such a circuit, simply structured information can preferably be transmitted and received, for example that data which can be linked with a special event, for example an emergency, can be transmitted. This information can preferably be derived from the measured signals, for example in the event of misuse, maladministration, excessively frequent or excessively infrequent dosing, under-dosing or overdosing of the oral administration form, energy emergency in or failure of the device. It is also possible to combine systems which are already applied in medication, such as implanted analgesic pumps or external perfusors, which control a monitored injection of pharmacological forms and wherein, under certain circumstances, a combination with further pharmacological forms should be avoided.

The receiving device can be any receiving device known to those skilled in the art which is supported by a public or non-public server, computer and/or network. The data received can be processed via a network comprising mobile radio devices, computers, workstations, small computers or any other computer or server, which conditions and/or stores this data, particularly preferably for the purpose of medical care. It may further be advantageous to use the device according to the invention in a public or non-public data management network, likewise preferably in data management or in a data management network within the context of therapy and/or diagnostics.

The data management network can be called up or used by experts. If, for example, an emergency is signalled, an expert, for example an emergency doctor, can be requested via an automated system, e.g. via a "computerized physician order entry system" (CPOE). The expert correlates the data collected by the data management network, in order to determine the location and time of the event, e.g. of the emergency, and in order to take suitable measures.

If the device according to the invention is used in therapy and/or diagnostics in accordance with the invention, the data management network can advantageously be equipped with a pharmacy computer or a pharmaceutical database, likewise advantageously with an expert system for medication.

The signals obtained by the device according to the invention and optionally transmitted can be processed, encoded and/or transmitted into the data management network in packed form. The data transmitted into this data network can be called up in a commercial route by means of a telephone call. The data transmitted can log the time-resolved disintegration of the magnetic body indirectly or directly, in real time and/or stored form, confirm said data or trigger further input requests in a manner known to those skilled in the art.

Data management networks for therapy and clinical developments are known and, by using expert systems, which are for example neural learning algorithms, produce higher data qualities and categories than the sum of the individual data. Higher data qualities from large statistical totals can be obtained, for example, on the basis of data reduction or maximum entropy algorithms.

When using the device according to the invention and/or when carrying out the method according to the invention in network systems, it is possible in particular to protect critical patients or individuals requiring care against misuse, erroneous application or other dangers in connection with the application of the magnetic body.

The device according to the invention can be used within the context of treatments, examinations, diagnoses and when researching new therapies and diagnoses, and within the context of linking medical technical systems.

Likewise, the device according to the invention can be used during the performance and monitoring of gastrointestinal active substance dosing, in particular in solid or solid-liquid combined preparations.

Furthermore, it may be advantageous to use this device for high throughput tests. With the aid of such tests, the integrity of the magnetic layers, phases and/or domains can be tested, and also the time behaviour during their dissolution in the human organism can be determined.

The invention claimed is:

1. A device, comprising
a detector system for registering magnetic bodies in the human organism, which detector system comprises:
at least two sensor arrangements with an instrument for recording the magnetic flux density measured by each sensor arrangement, wherein each sensor arrangement has one, two or three anisotropic magnetoresistance sensors, the axes of easy magnetization of which point in pair-wise different directions, and each sensor arrangement has a distance of 0.5 to 50 cm from the remaining sensor arrangement or sensor arrangements, and at least two sensor arrangements are tilted at an angle of between 0 and 45° with respect to one another, and
a log for registering a quantified evaluation before, during and/or after the registration of the magnetic body or bodies.

2. The device according to claim 1, wherein
the sensor arrangements are integrated in at least one strap, the clothing and/or an item of jewelry, or worn or affixed directly on the body by means of a suction cup or fastening aid, and
the log is carried on the body.

3. The device according to claim 1, wherein the log is a mobile computer, a mobile telephone, PDA, small computer, data logger with transmitter, and/or an input unit, and the log is electronically connected to the sensor arrangement.

4. A method for registering the magnetic flux density generated by a magnetic body in the human organism by means of a device according to claim 1, comprising:
(a) applying a set and reset pulse, at least once, to each anisotropic magnetoresi stance sensor,
(b) amplifying the signals of each AMR sensor by means of suitable
signal conditioning and by means of at least one low-pass filter,
(c) determining and recording the difference in the magnitudes of the vectors of the magnetic flux densities of each sensor arrangement,
and/or
determining and recording the angle Φ between the vectors from the measurement signals of the AMR sensors,
and,
(d) simultaneously with one of the steps (a), (b) or (c) or after a time T has elapsed following step (c),
registering the quantified evaluation, at least once, in the log, which is undertaken by the human wearer of the sensor arrangements.

5. The method according to claim 4, wherein the quantified evaluation is undertaken by virtue of the fact that a sense of well-being and/or physical fitness and/or at least one other subjective criterion, is assigned to alphanumerical signs or a grade scale, and entered into the log.

6. The method according to claim 5, wherein the values, obtained in step (c), for the difference
and/or for the angle $\Phi$ are recorded as a function of time and the evaluation, registered in step (d), is recorded as a function of time.

7. A method for registering oral administration forms and determining the time or times of the disintegration of the magnetic component in the digestive tract comprising registering magnetic bodies in a human organism with the device according to claim 1.

8. The method according to claim 7, wherein the measurement signals obtained are stored in a data storage device, and the stored data are optionally, upon reception of a request signal, transmitted to a receiving device.

9. A data management network comprising the device according to claim 1.

10. The method according to claim 7 wherein said human organism is in need of therapy and/or nutrition.

* * * * *